US005540796A

United States Patent [19]
Fries

[11] Patent Number: 5,540,796
[45] Date of Patent: Jul. 30, 1996

[54] PROCESS FOR ASSEMBLING ELASTICIZED EAR PORTIONS

[75] Inventor: Donald M. Fries, Combined Locks, Wis.

[73] Assignee: Kimberly-Clark Corporation, Neenah, Wis.

[21] Appl. No.: 286,086

[22] Filed: Aug. 3, 1994

[51] Int. Cl.⁶ .................................................. A61F 13/16
[52] U.S. Cl. ........................ 156/164; 156/229; 156/259; 156/264; 156/265; 156/267; 156/269
[58] Field of Search ....................... 156/324, 229, 156/164, 269, 267, 256, 259, 264, 265; 604/390, 386, 389, 391, 392

[56] References Cited

U.S. PATENT DOCUMENTS

| | | |
|---|---|---|
| 584,490 | 6/1897 | Warren . |
| 879,774 | 2/1908 | Jonata . |
| 1,096,477 | 5/1914 | Weisert . |
| 1,195,904 | 8/1916 | Bornstein . |
| 1,431,315 | 10/1922 | Le Moine . |
| 1,676,144 | 7/1928 | Houseknecht . |
| 2,025,843 | 12/1935 | Anderson . |
| 2,492,265 | 12/1949 | Bryan . |
| 2,516,951 | 8/1950 | Brink . |
| 2,545,761 | 3/1951 | Brink . |
| 2,564,094 | 8/1951 | Brandl . |
| 2,566,139 | 8/1951 | Ostrovsky et al. . |
| 2,739,594 | 3/1956 | Baten . |
| 2,830,589 | 4/1958 | Doner . |
| 3,322,122 | 5/1967 | Daniel . |
| 3,386,442 | 6/1968 | Sabee . |
| 3,400,718 | 9/1968 | Saijo . |
| 3,402,715 | 9/1968 | Liloia et al. . |

(List continued on next page.)

FOREIGN PATENT DOCUMENTS

| | | |
|---|---|---|
| 0059014B1 | 9/1982 | European Pat. Off. . |
| 0059015B1 | 9/1982 | European Pat. Off. . |
| 0217032A3 | 4/1987 | European Pat. Off. . |
| 0252413B1 | 1/1988 | European Pat. Off. . |
| 0339461B1 | 11/1989 | European Pat. Off. . |
| 0404648A1 | 12/1990 | European Pat. Off. . |
| 0487758A1 | 6/1992 | European Pat. Off. . |
| 0528282A2 | 2/1993 | European Pat. Off. . |
| 0532035A3 | 3/1993 | European Pat. Off. . |
| 2585217 | 1/1987 | France . |
| 2586558 | 3/1987 | France . |
| 63-123607 | 8/1988 | Japan . |
| 3-7815 | 1/1991 | Japan . |
| 4-61523 | 5/1992 | Japan . |
| 5137754 | 6/1993 | Japan .................................. 604/386 |
| 663077 | 3/1994 | Japan .................................. 604/390 |
| 2042342 | 5/1983 | United Kingdom . |
| 2268073 | 1/1994 | United Kingdom . |
| WO94/09736 | 5/1994 | WIPO . |

*Primary Examiner*—Jeff H. Aftergut
*Attorney, Agent, or Firm*—Paul Yee

[57] ABSTRACT

A distinctive technique for forming an elasticized article includes the steps of providing first and second webs of elasticized side panel material. The side panel material is constructed to be elastically stretchable at least along an appointed lateral cross direction. At least one first fastener is attached to the first web of side panel material, and at least one second fastener is attached to the second web of side panel material. A web of bridge material is provided with first and second side edge regions thereof. The first web of side panel material is attached to the first side edge region of the web of bridge material, and the second web of side panel material is attached to the second side edge region of the web of bridge material. The second web of side panel material is arranged to provide a cross-directional alignment between at least one corresponding, laterally opposed pair of the first and second fasteners. The web of bridge material and the first and second webs of side panel material are divided to provide at least one composite bridge assembly having a bridge member interconnecting a laterally opposed pair of first and second side panel members. The composite bridge assembly is secured to an appointed article web with the first and second side panels of the laterally opposed pair of side panel members located at opposite side regions of the article web.

22 Claims, 8 Drawing Sheets

U.S. PATENT DOCUMENTS

| | | | |
|---|---|---|---|
| 3,520,303 | 7/1970 | Endres . | |
| 3,561,446 | 2/1971 | Jones, Sr. | 604/390 X |
| 3,610,244 | 10/1971 | Jones, Sr. | 604/390 |
| 3,800,796 | 4/1974 | Jacob . | |
| 3,881,488 | 5/1975 | Delanty et al. . | |
| 3,900,031 | 8/1975 | Endres et al. . | |
| 3,901,236 | 8/1975 | Assarsson et al. . | |
| 3,930,501 | 1/1976 | Schaar . | |
| 4,024,867 | 5/1977 | Mesek | 604/390 |
| 4,047,528 | 9/1977 | Karami | 604/390 |
| 4,047,530 | 9/1977 | Karami | 604/390 |
| 4,076,663 | 2/1978 | Masuda et al. . | |
| 4,286,082 | 8/1981 | Tsubakimoto et al. . | |
| 4,578,071 | 3/1986 | Buell . | |
| 4,585,448 | 4/1986 | Enloe . | |
| 4,627,847 | 12/1986 | Puletti et al. . | |
| 4,663,220 | 5/1987 | Wisneski et al. . | |
| 4,699,622 | 10/1987 | Toussant et al. . | |
| 4,699,823 | 10/1987 | Kellenberger et al. . | |
| 4,701,170 | 10/1987 | Wilson et al. . | |
| 4,704,116 | 11/1987 | Enloe . | |
| 4,718,898 | 1/1988 | Puletti et al. . | |
| 4,738,677 | 4/1988 | Foreman . | |
| 4,743,246 | 5/1988 | Lawson . | |
| 4,753,646 | 6/1988 | Enloe . | |
| 4,778,458 | 10/1988 | Gronostajski . | |
| 4,795,510 | 1/1989 | Wittrock et al. . | |
| 4,816,025 | 3/1989 | Foreman . | |
| 4,861,652 | 8/1989 | Lippert et al. . | |
| 4,938,755 | 7/1990 | Foreman . | |
| 4,981,480 | 1/1991 | Gaudet et al. . | |
| 4,988,346 | 1/1991 | Pfefferkorn . | |
| 4,995,873 | 2/1991 | Knight . | |
| 5,019,073 | 5/1991 | Roessler et al. . | |
| 5,026,364 | 6/1991 | Robertson . | |
| 5,026,450 | 6/1991 | Cucuzza et al. . | |
| 5,028,224 | 7/1991 | Pieper et al. . | |
| 5,069,678 | 12/1991 | Yamamoto et al. . | |
| 5,147,343 | 9/1992 | Kellenberger . | |
| 5,147,347 | 9/1992 | Huang et al. . | |
| 5,176,670 | 1/1993 | Roessler et al. . | |
| 5,187,817 | 2/1993 | Zolner | 604/389 X |
| 5,192,606 | 3/1993 | Proxmire et al. . | |
| 5,226,992 | 7/1993 | Morman . | |
| 5,269,776 | 12/1993 | Lancaster et al. . | |
| 5,358,500 | 10/1994 | Lavon et al. | 604/385.2 |
| 5,399,219 | 3/1995 | Roessler et al. | 156/229 X |

PROCESS FOR ASSEMBLING ELASTICIZED EAR PORTIONS

FIELD OF THE INVENTION

The present invention relates to a method for forming an elasticized article. More particularly, the invention relates to a method for forming an article wherein elasticized side panel webs are connected to a web of bridge material to provide for a composite bridge member which can be more efficiently assembled into the article.

BACKGROUND OF THE INVENTION

Conventional absorbent articles, such as disposable diapers, have been constructed with elasticized waistbands. Particular article designs have incorporated a stretchable outer cover composed of an elastomeric web material, such as a stretch bonded laminate which includes a layer of nonwoven fabric. Other conventional designs have included elastomeric side panel members connected to the lateral side edges of a polymer film material. For example, see U.S. Pat. No. 4,861,652 to Lippert et al.; U.S. Pat. No. 4,701,170 issued Oct. 20, 1987, to Wilson et al.; and U.S. Pat. No. 5,019,073 issued May 28, 1991, to Roessler et al.

Conventional techniques for forming articles with elasticized side panel portions have not been adequate for incorporation into high speed manufacturing systems. It has, for example, been difficult to maintain a desired cross-directional spacing and/or alignment between the elastomeric panels positioned at opposed side edges of the article. In addition, the conventional techniques have not provided adequate control of the side panel members during the manufacturing process. Undesired movements of the elastomeric side panel members and other components or component assemblies can undesirably interfere with the manufacturing process.

BRIEF DESCRIPTION OF THE INVENTION

A process aspect of the invention provides a method for forming an elasticized article which includes the steps of providing first and second webs of elasticized side panel material. The side panel material is constructed to be elastically stretchable at least along an appointed lateral, cross-direction. At least one first fastener is attached to the first web of side panel material, and at least one second fastener is attached to the second web of side panel material. The first web of side panel material is attached to a first side edge region of a web of bridge material, and the second web of side panel material is attached to a second side edge region of the web of bridge material. The second web of side panel material is arranged to provide a cross-directional alignment between at least one corresponding, laterally opposed pair of the first and second fasteners. The web of bridge material and the first and second webs of side panel material are divided to provide at least one composite bridge assembly having a bridge member interconnecting a laterally opposed pair of firsts and second side panel members. The composite bridge member is secured to an article web with the first and second side panel members located at opposite side regions of the article web.

A further aspect of the process of the invention can further include the steps of providing a web of backsheet material, and positioning at least one absorbent body at a selected location along a machine-direction length of the backsheet web. A web of topsheet material is provided to sandwich the absorbent body between the web of backsheet material and the web of topsheet material. At least one composite bridge assembly is connected to at least one of the backsheet and topsheet layers with the bridge material arranged in an overlapping relation with a longitudinal end section of the absorbent body.

In its various aspects, the process of the invention can more efficiently produce elasticized articles at high speed. The process can provide a more accurate placement of elasticized side panel material at the appointed waistband edges of each appointed article segment. There can be a more accurate alignment of the fasteners at laterally opposed side regions of each appointed article. Where the fastening mechanisms employ adhesive securement, the fasteners can be better protected from contamination. The various aspects of the article of the invention can advantageously provide improved resistance to leakage, particularly leakage at the waistband regions of the article. The articles can have mope consistent quality and can provide more consistent performance due to the more accurate and secure placement and cross-directional alignment between the opposed pair of elastomeric side panels. In addition, the more accurate and secure placement and alignment of the fasteners can provide improved appearance and fit on the wearer.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The method and apparatus of the present invention will be described herein in relationship to their use in disposable absorbent articles, but it should be understood that potential uses of the method and apparatus of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for re-use. The articles can be placed against or in proximity to the body of a wearer to absorb and contain various exudates discharged from the body. While the present description will particularly tie made in the context of a diaper article, it should be understood that the present invention is also applicable to other disposable personal care absorbent articles, such as adult incontinence garments, sanitary napkins, children's training pants, and the like.

The present invention can advantageously be employed to more efficiently produce improved absorbent articles having a front waistband section, a rear waistband section and an intermediate section which interconnects the front and rear waistband sections. The article includes a backsheet layer having a laterally extending width and a longitudinally extending length. A liquid permeable topsheet layer is superposed on the backsheet layer, and the topsheet layer has a laterally extending width and a longitudinally extending length. An absorbent body is located between the backsheet layer and the topsheet layer, and an elasticized side panel is connected to the article at each laterally opposed end region of at least one of the front and rear waistband sections. The side panels are constructed to be elastically stretchable at least along a lateral, cross-direction of the article. A bridge member, which is separate from the backsheet and topsheet layers, extends laterally to interconnect between the elasticized side panels. The bridge member can be arranged in an overlapping relation with a longitudinal end section of the absorbent body, and is operably connected to at least one of the backsheet and topsheet layers. A fastening means for securing the article on a wearer is connected to a laterally distal end region of at least one, and preferably both, of the side panels. Various configurations of such articles are described in U.S. patent application Ser. No. 286,491 of D. Fries et al., entitled ABSORBENT ARTICLE WITH ELASTICIZED SIDE PANELS CONNECTED BY A BRIDGE MEMBER and filed Aug. 3, 1994 (Attorney docket No. 11,426), the disclosure of which is hereby incorporated by reference in a manner that is consistent (not contradictory) herewith.

Figure 1:
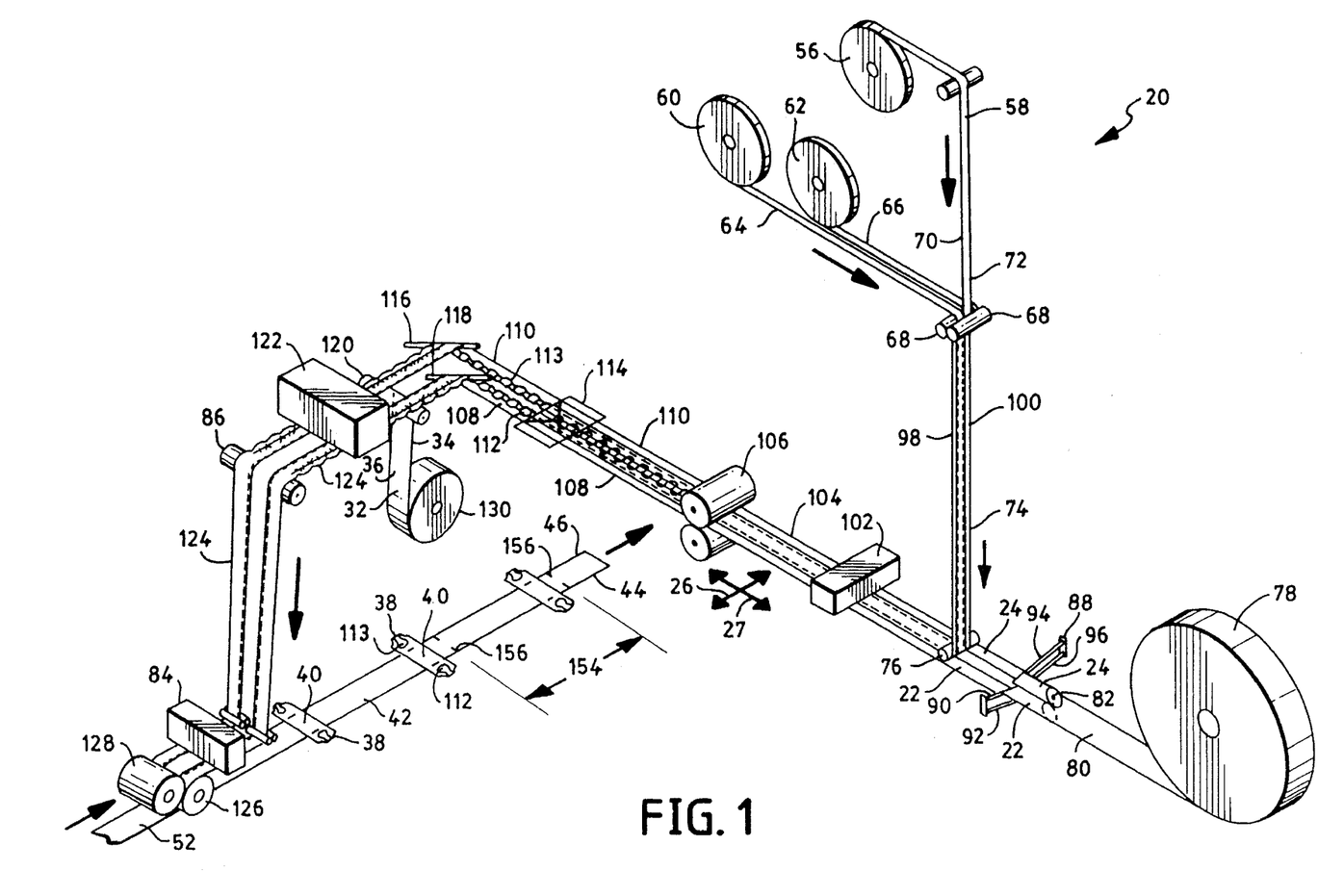
FIG. 1 representatively shows a schematic of a process of the invention configured to position a bridge member adjacent a major facing surface, such as an outerside surface, of the backsheet web layer.

With reference to FIG. 1, a process aspect of the invention shown generally at 20 provides a distinctive method for forming an elasticized article, such as an elasticized disposable diaper. The method includes the steps of providing a first web of elasticized side panel material 22 and a second web of elasticized side panel material 24. The side panel material is constructed to be elastically stretchable at least along an appointed lateral cross- direction of the process. At least a first fastener, such as fastening tab 112, can be attached to the first web of side panel material 22, and at least a second fastener, such as fastening tab 113, can be attached to the second web of side panel material 24. A web of bridge material has a first side edge 34 and a second side edge 36. In the shown configuration, the web of bridge material is a web constructed separate from the other components of the diaper article, and the web of bridge material is operably provided into the process. The first web of side panel material 22 is attached to the first side edge region 34 of the web of bridge material 32. Similarly, the second web of side panel material 24 is operably attached to the second side edge region 36 of the web of bridge material 32. The second web of side panel material is arranged to provide a cross-directional alignment between at least one corresponding, laterally opposed pair of the first and second fasteners 112 and 113, respectively. The web of bridge material 32 and the first and second webs of side panel material 22 and 24 are divided to provide at least one composite bridge assembly 38 having a bridge member 40 interconnecting the laterally opposed pair of first and second side panel members 28 and 30. The composite bridge assembly is secured to an article web in a configuration wherein the first side panel member 28 and the second side panel member 30 of the laterally opposed pair of side panel members are located at opposite side regions 44 and 46 of the article web 42. In particular, the opposed pair of side panel members are substantially aligned along the cross-deckle direction 26 of the process and apparatus. Fastening means, such as provided by the fastening tabs 112 and 113, are operably attached to the laterally distal end regions of the respective side panels to provide a mechanism for securing the article on a wearer.

In another aspect, the method of the invention divides the web of bridge material 32 and the attached first and second webs of side panel material 22 and 24 to provide a plurality of individual, composite bridge assemblies 38. Each bridge assembly has a bridge member 40 which interconnects at least one laterally opposed pair of the first and second side panel members. The plurality of composite bridge assemblies are secured to the article web 42 at a plurality of predetermined space locations along the machine direction 27 of the process. The composite bridge assemblies are positioned and arranged with each of the laterally opposed pairs of first and second side panel members arranged to provide a first side panel located at side region 44 of the article web 42 and second side panel located at a laterally opposite, side region 46 of the article web.

A further process aspect of the method of the invention includes the steps of providing a web of backsheet material 48 (FIG. 2), and positioning at least one absorbent body at a selected location along the machine direction length of the backsheet web. A web of topsheet material 52 is provided to sandwich the absorbent body 50 between the web of backsheet material 48 and the web of topsheet material 52. At least one composite bridge assembly 38 is connected to at least one of the backsheet and topsheet webs with at least a portion of the bridge material arranged in an overlapping relation with a longitudinal end section 54 of the at least one absorbent body 50.

Articles which include elastomeric side panels and selectively configured fastener tabs are described in U.S. patent application Ser. No. 168,615 of T. Roessler et al., entitled DYNAMIC FITTING DIAPER, and filed Dec. 16, 1993 (Attorney docket No. 10,961). The fastening systems can include a stress beam member for distributing applied stresses the area of the side panel material, and can include fastening tabs which incorporate a necked down intermediate region in combination with a relatively wider, user-bond section thereof. Various techniques for forming the desired fastening systems are described in U.S. patent application Ser. No. 200,593 of T. Roessler et al., entitled METHOD FOR MAKING A FASTENING SYSTEM FOR A DYNAMIC FITTING DIAPER and filed Feb. 23, 1994 (Attorney docket No. 11,186). The disclosures of these documents are incorporated herein by reference in a manner that is consistent herewith.

As illustrated in FIG. 1, the representatively shown process generally has a cross-deckle direction 25 and a machine-direction 27. At any particular, selected location along the process, the machine-direction is the generally length-wise direction along which a particular web (or composite web) of material is moving through the process. The cross-direction extends generally along the plane of the web of material and is perpendicular to the particular machine-direction established by the process at the selected location.

The shown arrangement of the method of the invention includes a supplying means, such as supply roll 56, for delivering a web of attachment tape substrate material 58. The substrate web has first and second side edge regions 70 and 72 which are oppositely positioned along the cross-deckle direction of the substrate web. The substrate web may be composed of various suitable materials. For example, the shown embodiment of the substrate web can be composed of polypropylene. Suitable materials are available from Avery Corp., a business having offices located in Painesville, Ohio.

A further supplying means, such as supply roll 60, supplies a first web of release tape material 64, and another supply means, such as supply roll 62, provides a second web of release tape material 66. The two release tape webs 64 and 66, and the substrate web 58 are delivered to an assembly means, such as the nip region between the pair of rollers 68, for operable interconnection. In particular, release tape web 64 is connected to the first side edge region 70 of substrate web 58, and the second release tape web 66 is connected to the second side edge region 72 of the substrate web.

The release tape webs may be composed of various suitable materials. For example, the shown embodiment of the release tape webs can be composed of polypropylene. Suitable materials are available from Avery Corp., a business having offices located in Painesville, Ohio. Each release tape web has a coating of low-adhesion release material on one of its major facing surfaces, and can include a layer of adhesive on its opposite adhesion surface to provide a desired bonding to one or more other components, such as substrate web 58 or side panel webs 22 and 24.

The shown embodiment of substrate web 58 includes a layer of primary adhesive distributed onto a major facing surface thereof, and the primary adhesive can be employed to produce the desired interconnections between the substrate web 58 and the pair of release tape webs 64 and 66. Alternatively, other types of connecting means, such as thermal bonds, sonic bonds, mechanical stitching, stapling, and the like or combinations thereof, may be employed. The resultant assembly comprising substrate web 58 and release tape weds 64 and 66 provide a first composite web 74 in which the release-coated surfaces of the release tapes are in a generally exposed position. The composite web 74 is operably directed to a guiding means, such as guide roller 76 for further processing.

An additional supplying means, such as supply roll 78, provides a web of side panel material 80. A suitable separating mechanism, such as slitter 82, is employed to divide the supply web 80 into a first web of side panel material 22 and a second web of side panel 24. In the illustrated configuration, for example, slitter 82 can separate supply web 80 into first and second side panel webs which have substantially equal cross-directional widths. Optionally, the separated side panel webs and have unequal cross-directional widths to provide desired benefits.

In particular configurations of the invention, the side panel material is composed of an elastomeric material which is elastomerically stretchable at least along the cross-deckle direction 26 of the supply web 80. The material of supply web 80 can, for example, a stretch-bonded-laminate (SBL) material, a neck-bonded-laminate (NBL) material, an elastomeric film, an elastomeric foam material, or the like. For example, suitable meltblown elastomeric fibrous webs for forming side panels 28 and 30 are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application EP No. 0 110 010 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to M. Mormon, the disclosure of which is hereby incorporated by reference. A particular neck-bonded-laminate (NBL) can be composed of a film of elastomer material sandwiched between two layers of spunbond material. The film can be composed of a KRATON® elastomer available from Shell Oil Company, and the spunbond layers can be composed of spunbond, polypropylene fibers.

The relative positioning of the first and second webs of side panel material is adjusted to a desired spacing along the cross-deckle direction of the process by an operable spreader mechanism 88. In the illustrated embodiment, for example, the spreader mechanism can include a conventional system of turn bars which reposition and relocate the first and second webs of side panel material at a desired spacing therebetween. In particular, the spreader mechanism 88 can include a first pair of turn bars 90 and 92 which are tilted and canted in a manner well known to the art to produce the desired repositioning of first side panel 22. The first side panel web 22 moves in an S-shaped path to pass over turn bar 90 and under turn bar 92, and becomes offset by a predetermined distance away from second side panel web 24.

Similarly, a conventional set of turn bars 94 and 96 are tilted and canted at appropriate angles in a manner well known in the art to reposition second side panel web 24. In particular, the second side panel web moves in another S-shaped path to pass over turn bar 94 and under turn bar 96 in a manner which directs a second side panel web 24 to a position that is spaced the desired distance away from first side panel web 22.

After the spreader mechanism has generated the desired cross-deckle spacing between first side panel web 22 and second side panel web 24, the two side panel webs are directed to the guiding means provided by guide roller 76. Guide roller 76 operably directs composite web 74 into a desired positioning relative to the first and second side panel webs 22 and 24 to allow an operable interconnection between the side panel webs and the composite web 74. Composite web 74 includes a first side edge region 98 and a second side region 100. The first side edge region 98 of composite web 74 is connected to a side edge region of first side panel web 22, and the second side edge region 100 of the composite web 74 is connected to an appointed side edge region of second side panel web 24. In the illustrated embodiment, for example, an attaching means such as an ultrasonic bonder 102 can be employed to operably secure the appointed side regions of composite web 74 to the first and second panel webs 22 and 24 to produce a second composite panel web 104. The appointed side sections of first and second panel webs 22 and 24 can be overlapped with and attached to the appointed side regions of composite web 74. In other aspects of the invention, an adhesive located at side regions 98 and/or 100 can be employed to secure the composite web 74 to either or both of the side panel webs 22 and 24. The adhesive can, for example, be carried on the adhesion surface of the release tapes 64 and 66. If desired, a combination of adhesive and sonic bonds can be employed to secure the composite web 74 to the side panel webs 22 and 24.

Panel web 104 is operably directed into a separating means, such as a die cutting system 106, to longitudinally divide the panel web 104 into a pair of composite fastener webs 108 and 110. The die cutter produces an undulating, serpentine division line which is positioned along a medial section of panel web 104. The serpentine line extends generally along the length dimension of panel web 104 and includes alternately traversing, side-to-side sections thereof. The traversing sections of the dividing line include retroceding portions thereof to provide for the individual, distinctively shaped fastening tabs 112. Additional details regarding the construction of the fastening tabs and fastening system are set forth in detail in the above-described U.S. patent application Ser. No. 168,615 of T. Roessler et al. which is entitled "DYNAMIC FITTING DIAPER" and was filed Dec. 16, 1993.

The fastener webs 108 and 110 are operably directed to a system of conventional folding boards 114 to reposition the individual fastening tabs into a storage position against an appointed surface of its associated fastener web 108 or 110, as appropriate. A phase adjusting means, such as provided by alignment turn bars 116 and 118, operably repositions the lengthwise, machine-directional phasing of the fastener tabs on first fastener web 108 relative to the fastener tabs on second fastener web 110. In particular, the method is configured to operably arrange appointed, corresponding pairs of fastening tabs 112 into a substantial cross-deckle alignment along the cross-direction of the process. Accordingly, the process provides at least one corresponding, laterally opposed pair of fasteners, which includes a first fastener from the first fastener web 108 and a second fastener from the second fastener web 110. In the illustrated embodiment, the process is advantageously constructed to provide a multiplicity of corresponding, laterally opposed pairs of the first and second fasteners.

The substantially aligned first and second fastener webs 108 and 110 are directed to a suitable assembling mechanism, such as assembly roller 120, and a supplying means, such as bridge material supply roll 130, provides a separate web of bridge material 32 to assembly roller 120 for connection with the first and second fastener webs 108 and 110. A suitable attaching means, such as an ultrasonic bonder 122 operably secures the first fastener web 108 to a first side edge region 34 of bridge web 32, and operably secures second fastener web 110 to a second side edge region 36 of the bridge web 32. A directing means, such as a mechanism including guide roller 86, operably directs the resultant, bridge assembly composite web 124 to a second attaching means, such as adhesive applicator 84. The adhesive applicator applies a suitable adhesive, such as a conventional hotmelt adhesive, for securing predetermined segments of the bridge assembly web 124 onto an appointed component web, such as the illustrated topsheet web material 52. The adhesive is operably constructed and arranged to provide an operable securement between the bridge assembly segments and the appointed component web. The present invention can be configured to attach individual bridge assemblies 38 onto a major body-facing side or outward-facing side of the topsheet web 52, as desired. Alternatively, the present invention can be configured to attach individual bridge assemblies 38 onto a major body-facing side or outward-facing side of a backsheet web 48 (FIG. 2), as desired.

In the various aspects of the invention, the method can be configured to provide a bridge web 32 which is constructed to be substantially impermeable to the passage of liquid through its thickness dimension. In alternative configurations, the method can be configured to provide a bridge web material which is permeable to a passage of gas, such as air, through its thickness dimension. The gas permeable materials may also be constructed to have a selected level of resistance to the passage of aqueous liquids, such as urine, therethrough. Optional arrangements of the method can be configured to provide a bridge web material which is substantially elastomeric. Such elastomeric materials can, for example, be similar to the materials employed to construct side panel webs 22 and 24.

A suitable cutoff means such as rotary cutter 128 is employed to separate bridge assembly web 124 into segments of desired size. The rotary cutter 128 divides the web of bridge material 32 and the first and second webs of side panel material 22 and 24, and also divides any associated component webs, such as release tape webs 64 and 66 and fastener substrate web 58. The dividing operation thereby provides at least one composite bridge assembly 38 having a bridge member 40 interconnecting the aligned, laterally opposed pair of first and second fasteners 112 and 113. In the illustrated embodiment, for example, the composite bridge assembly web 124 is divided into a plurality of individual, composite bridge assemblies 38.

A phased, cut-and-place, intermittent assembling means, such as a mechanism comprising a conventional vacuum slip roll 126 and a rotary knife and anvil system 128, can be employed to connect at least one composite bridge assembly 38 to at least one of the component webs, such as topsheet web 52 and/or backsheet web 48. In the illustrated embodiment, for example, the cut-and-place assembling mechanism is constructed and arranged to operably connect a sequential plurality of the bridge assemblies 38 to the selected component web at a plurality of predetermined, spaced-apart locations along the machine-direction of the desired component web.

An example of a suitable arrangement of rotary cutter 128 and vacuum slip roll 126 is described in U.S. Pat. No. 4,795,510 issued Jan. 3, 1989 to M. Wittrock et al. and entitled "PROCESS FOR APPLYING REINFORCING MATERIAL TO A DIAPER COVER MATERIAL" (Attorney docket No. 8366), the disclosure of which is hereby incorporated by reference in a manner that is consistent herewith.

The resultant article web 42 defines an interconnected plurality of individual article segments 154. A conventional cutting mechanism (not shown) can then separate the article web 42 along preselected division lines 156 to produce selected individual articles.

Figure 2:
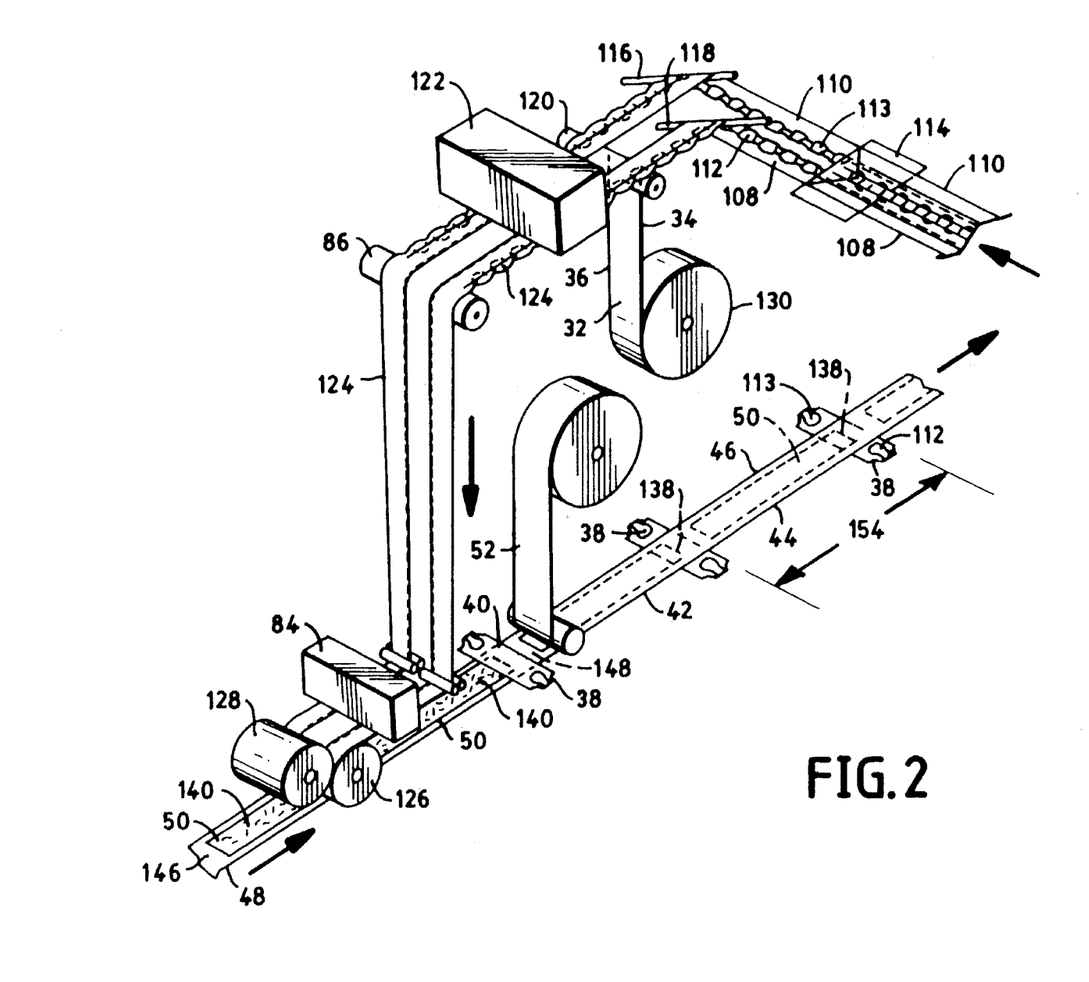
FIG. 2 representatively shows a schematic of the process of the invention configured to place a bridge member generally adjacent an outwardly facing surface of the topsheet web layer.
Figure 3:
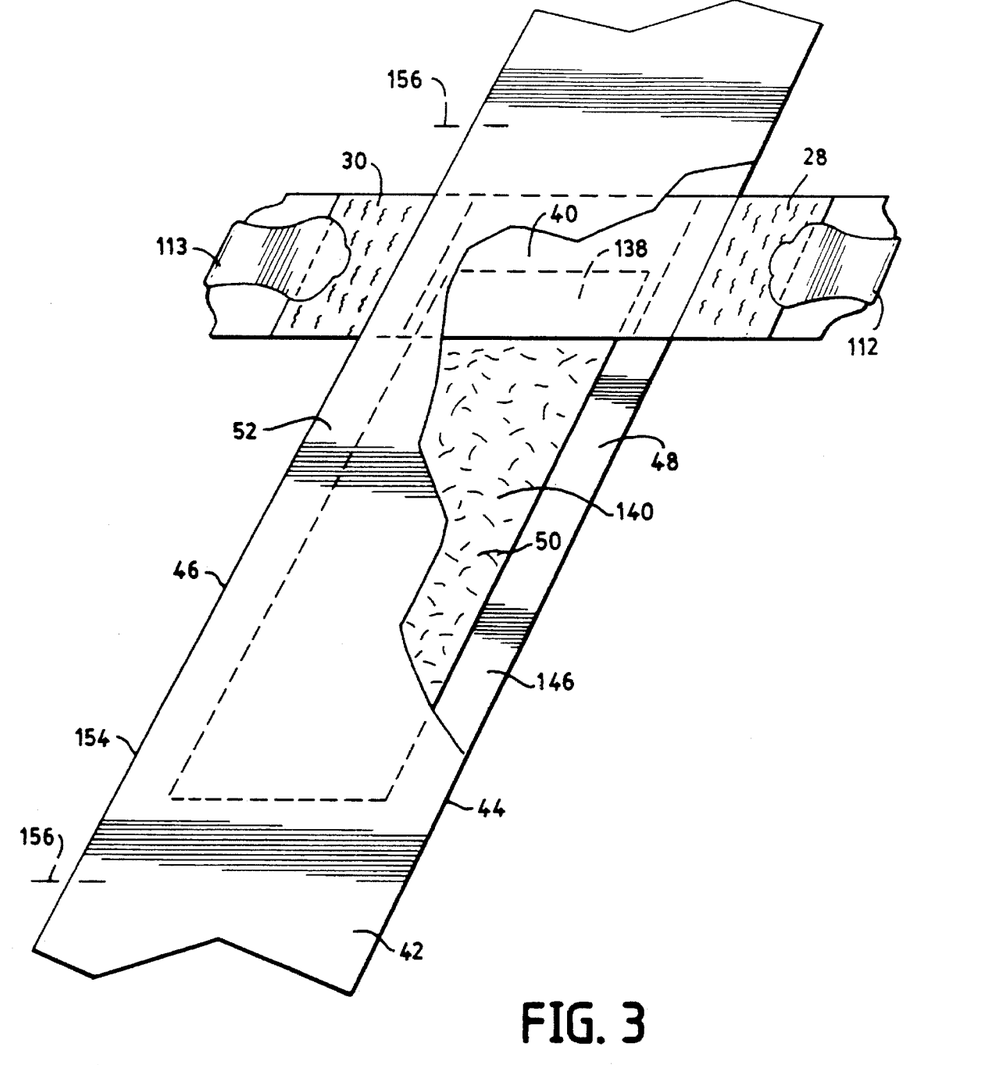
FIG. 3 representatively shows a perspective view of an article web produced by the process of the invention illustrated in FIG. 2.

With reference to FIGS. 2 and 3, the invention can include the steps of providing a web of backsheet material 48, and positioning at least one absorbent body 50 at a selected location along a machine directional length of the backsheet web. In the illustrated embodiment, for example, a plurality of absorbent bodies 50 can be positioned at predetermined, regularly spaced locations along the length of the backsheet web. A web of topsheet material 52 sandwiches the absorbent body between the web of backsheet material 48 and the web of topsheet material 52. At least one composite bridge assembly 38 is connected to at least one of the backsheet and topsheet webs with at least a portion of the bridge member material arranged in an overlapping relation with a longitudinal end section 138 of the correspondingly associated absorbent body 50.

As representatively shown in FIGS. 2 and 3, a particular aspect of the invention can include the steps of securing the composite bridge assembly 38 between the backsheet web 48 and the topsheet web 52, and arranging at least a portion of the bridge member material 40 to be in a contacting, immediately adjacent relation to an inward, bodyside surface 140 of the absorbent body 50. Thusly configured, the bridge member can be covered by topsheet web 52, and can operate as an internal dam over the edge of its corresponding absorbent body 50.

As discussed above, FIG. 2 particularly illustrates a process of the invention configured to connect the bridge assemblies 38 to an inwardly facing bodyside surface 146 of backsheet web 48. It should be readily apparent that the process can alternatively be configured to connect the bridge assemblies 38 to an opposite, outerside surface 148 of the backsheet web.

Figure 4:
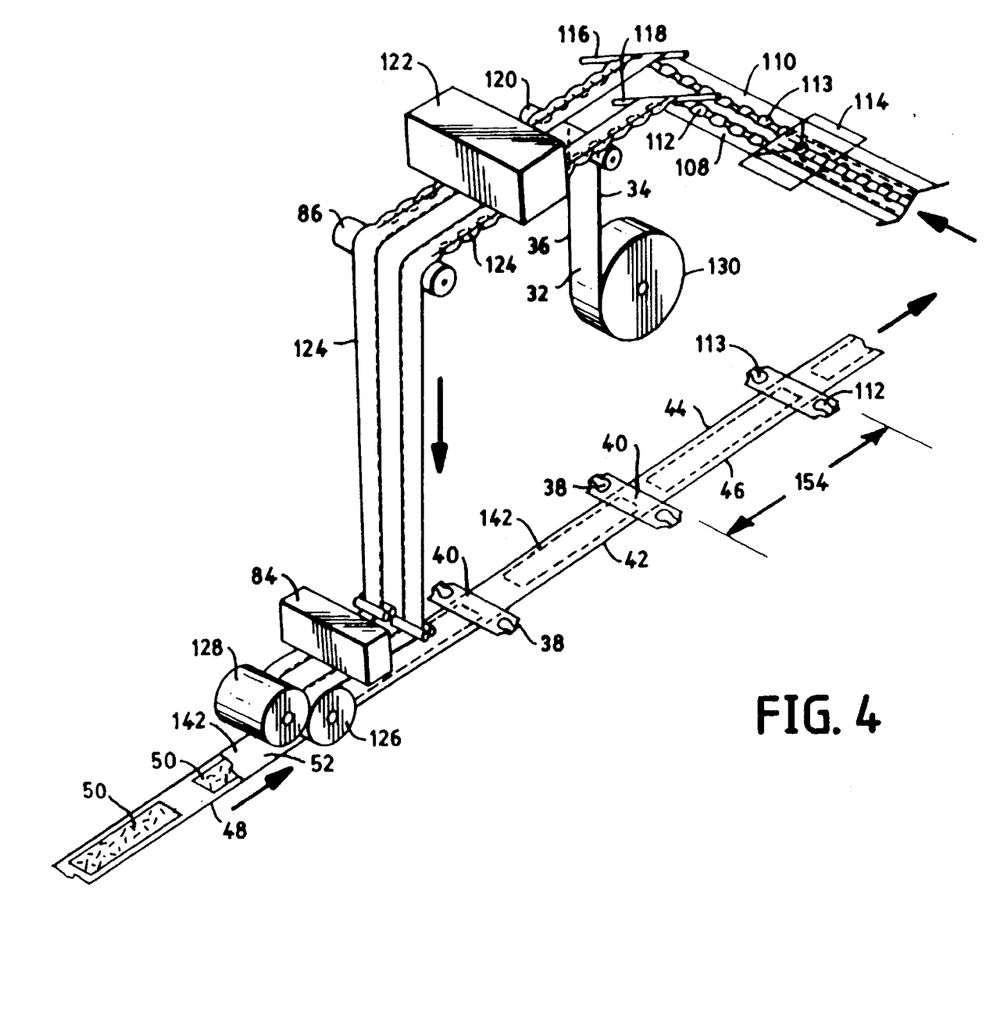
FIG. 4 representatively shows a schematic of the process of the invention configured to position a bridge member adjacent a bodyside surface of the topsheet web layer.
Figure 5:
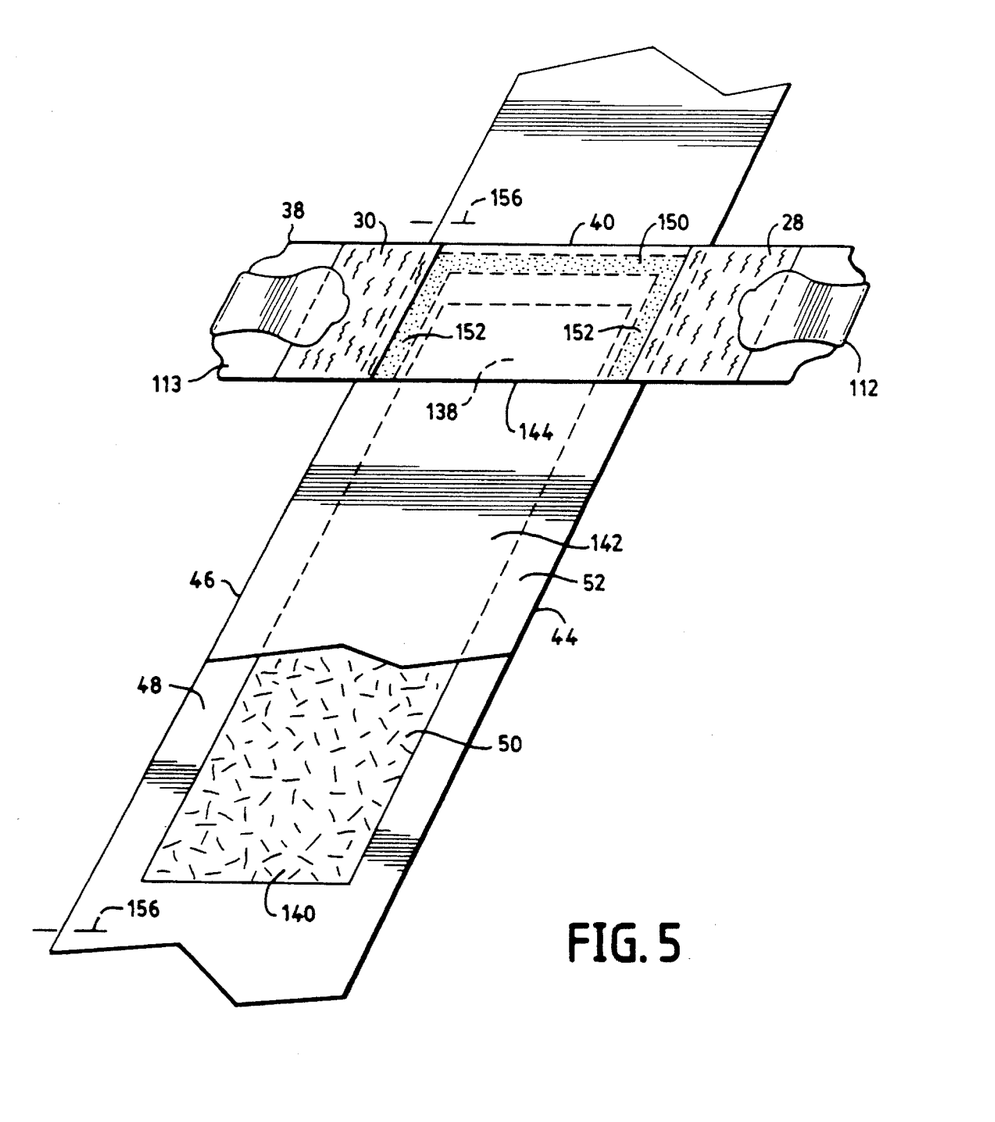
FIG. 5 representatively shows a perspective view of an article web produced by the process of the invention illustrated in FIG. 4.

With reference to FIGS. 4 and 5, a further aspect of the invention can include the step of securing the composite bridge assembly 38 in a substantially adjacent facing relation with a major, bodyside surface 142 of topsheet web 52. In particular configurations, the bridge member 40 and/or composite bridge assembly 38 can be attached in an arrangement which leaves a longitudinally-inboard edge portion 144 of bridge member 40 substantially free and unattached. In the shown embodiment, for example, bridge member 40 can include a longitudinally-outboard, laterally extending edge region 150 which is substantially fixed in position, a pair laterally-outboard, longitudinally extending edge regions 152 which are substantially fixed in position, and the movable edge 144. The appointed edge regions 150 and 152 are operably attached to the immediately contacting portions of topsheet 52. In particular configurations, the attachments of the edge regions 150 and 152 are constructed to provide an operable seal which can substantially prevent undesired leakage of liquid past the edge region attachments. At least a portion of the longitudinally-inboard edge region 144 of bridge member 40 is substantially free and movable. In the shown embodiment, for example, a medial section of inboard edge 144 is movable.

Figure 6:
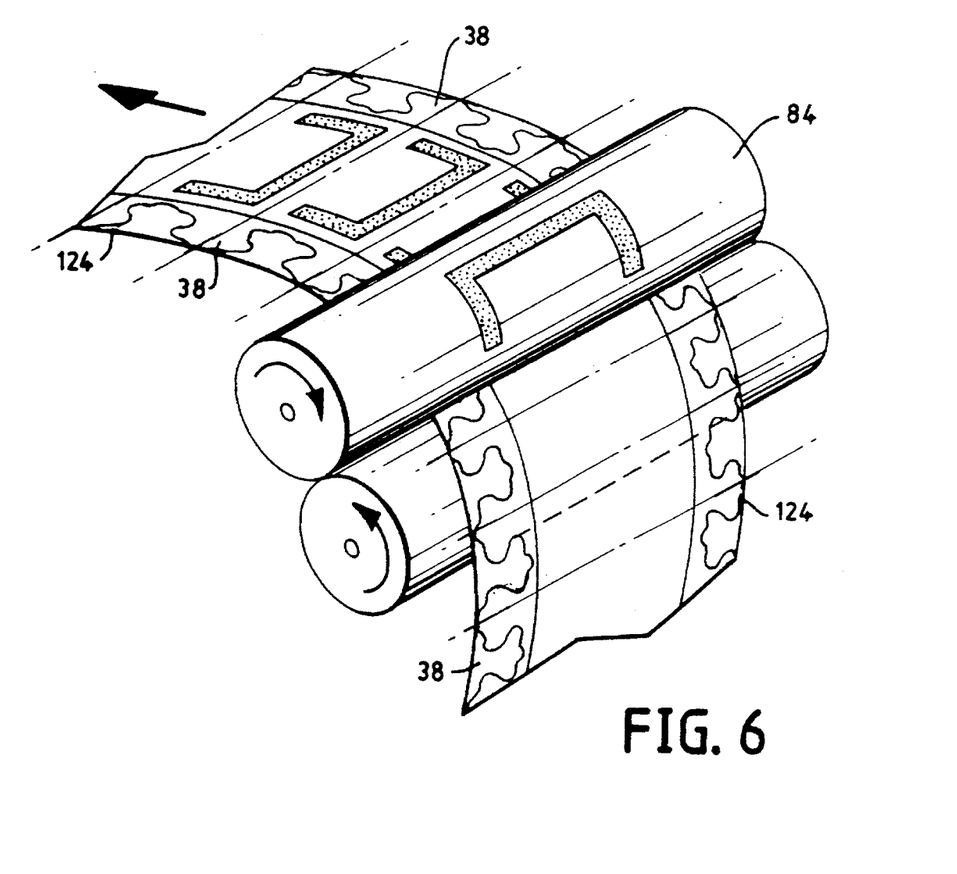
FIG. 6 representatively shows a schematic of the process of the invention configured to apply onto each appointed bridge member a shaped pattern area of adhesive which attaches the bridge member into the assembled article.

Various techniques, such as adhesive bonding, thermal bonding, ultrasonic bonding and the like, as well as combinations thereof, can be employed to form the attachments at edge regions 150 and 152. With reference to FIG. 6, for example, a desired pattern shape of adhesive can be applied to each of the appointed bridge assemblies 38 which are interconnected to one another in series along the composite bridge assembly web 124. The adhesive can be applied by spraying, printing, pattern extrusion or the like. In the illustrated embodiment, for example, the adhesive applicator 84 can be configured to print the desired adhesive pattern onto each bridge assembly 38 by employing conventional printing mechanisms.

Figure 7:
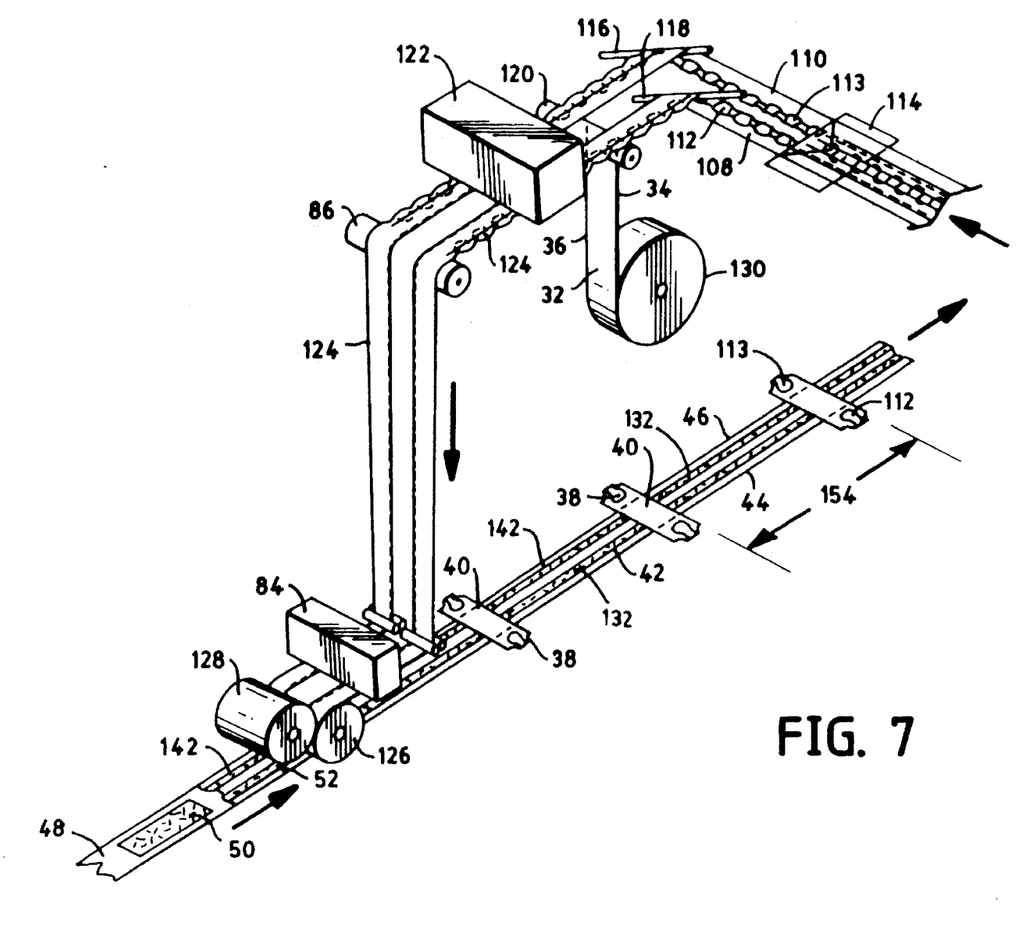
FIG. 7 representatively shows a schematic of the process of the invention configured to position a bridge member adjacent a bodyside surface of the topsheet web layer in an arrangement overlying the bodyside surfaces of a pair of longitudinally extending containment flaps.
Figure 8:
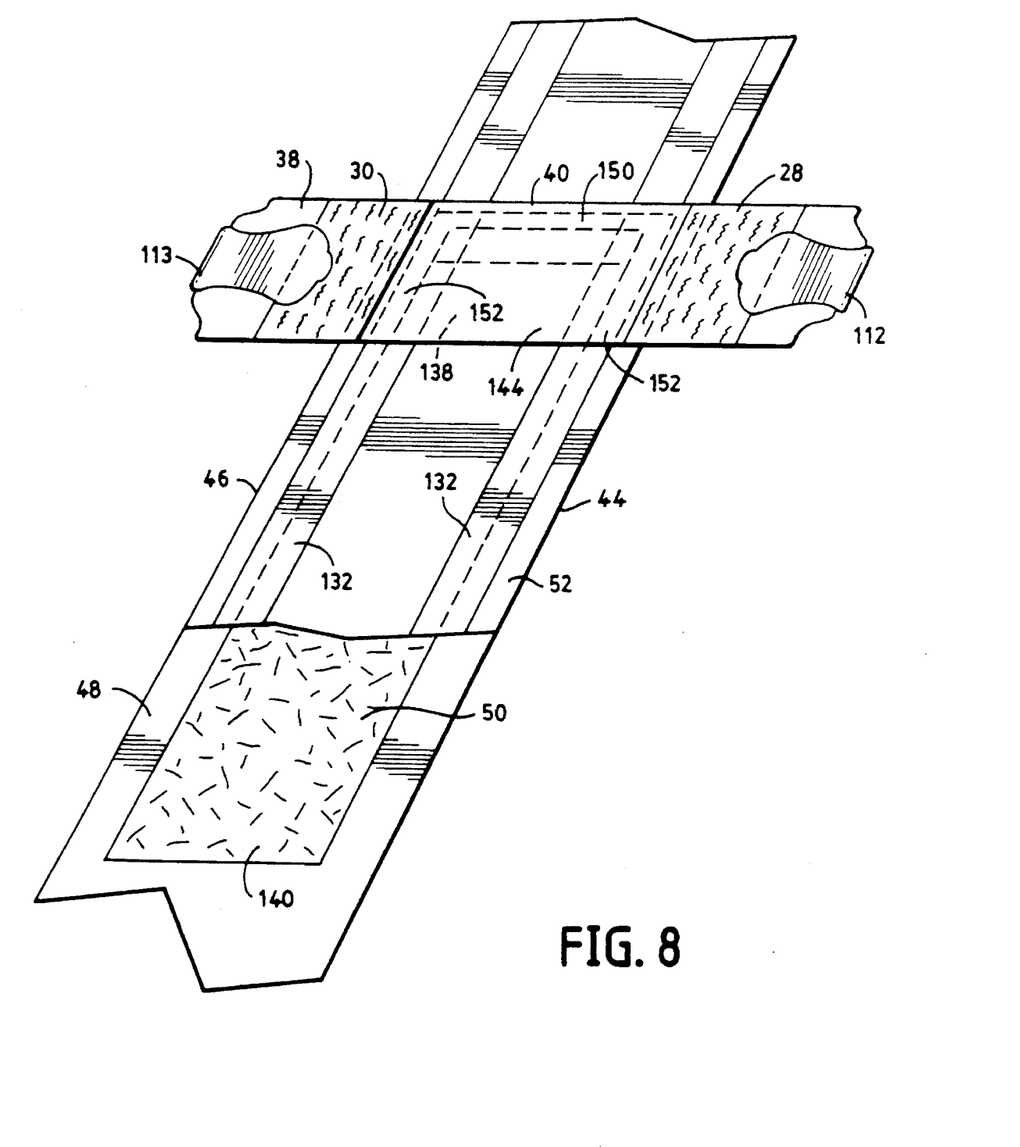
FIG. 8 representatively shows a perspective view of an article web produced by the process of the invention illustrated in FIG. 6.

With reference to FIGS. 7 and 8, other aspects of the invention can include the step of attaching at least a pair of lengthwise extending elasticized containment flaps 132 to the bodyside surface 142 of topsheet web 52. Suitable containment flap configurations are described in detail in U.S. Pat. No. 4,704,116 issued Nov. 11, 1987 to K. Enloe and entitled DIAPERS WITH ELASTICIZED SIDE POCKET, the disclosure of which is hereby incorporated by reference in a manner that is consistent herewith. Other containment flap configurations are described in U.S. patent application Ser. No. 206,816 of R. Everett et al., entitled ABSORBENT ARTICLE HAVING AN IMPROVED SURGE MANAGEMENT and filed Mar. 4, 1994 (Attorney docket No. 11,375), the disclosure of which is hereby incorporated by reference in a manner that is consistent herewith.

The process of the invention can then be configured to include the step of operably attaching the composite bridge assembly 38 to the bodyside surface 142 of topsheet web 52 and, optionally, to selected portions of the containment flaps 132. In such arrangements of the invention, at least a portion of the bridge member material 40 can be constructed to overlie appointed sections of the containment flaps, and to occupy a position interposed between the containment flaps 132 and the body of the wearer. As previously described, the bridge member 40 and/or composite bridge assembly 38 can be attached to provide an arrangement which leaves an inboard edge portion 144 of bridge member 40 substantially free and unattached. Optionally, the attachments can provide a sealing engagement to inhibit leakage. The bridge member free edge 144 can generally span substantially the entire cross-directional distance between at least the moveable edge sections of the containment flaps. In optional configurations, selected portions of the lateral end regions of the inboard edge can be attached to the corresponding, immediately adjacent sections of topsheet 52 and/or to immediately adjacent sections of the containment flaps 132. The resultant bridge member can cooperate with the containment flaps to provide a further improved containment pocket along the rear waistband portion of the final article.

In the various aspects of the invention, article web 42 can define an interconnected, serial plurality of article segments 154. Accordingly, the process of the invention can further include the step of separating the article web along predetermined division lines 156 to provide individual articles, such as individual disposable diapers. Examples of the diaper articles are representatively shown in U.S. patent application Ser. No. 286,491 of D. Fries et al., entitled ABSORBENT ARTICLE WITH ELASTICIZED SIDE PANELS CONNECTED BY A BRIDGE MEMBER and filed Aug. 3, 1994 (Attorney docket No. 11,426), the disclosure of which is hereby incorporated by reference in a manner that is consistent herewith. The separating step can be performed by employing any conventional cutting mechanism, such as a rotary cutter or the like.

Having described the invention in rather full detail, it will be readily apparent that various changes and modifications can be made without departing from the spirit of the invention. All of such changes and modifications are contemplated as being within the scope of the invention as defined by the subjoined claims.

What is claimed is:

1. A method for forming an elasticized article, comprising the steps of:

(a) providing first and second webs of elasticized side panel material, said side panel material constructed to be elastically stretchable at least along an appointed lateral, cross-direction, said providing step including the steps of dividing a supply web into said first and second webs of elasticized side panel material, and positioning said first and second webs to a desired spacing therebetween;

(b) attaching at least one first fastener to said first web of side panel material;

(c) attaching at least one second fastener to said second web of side panel material;

(d) providing a web of bridge material having first and second side edge regions thereof;

(e) attaching said first web of side panel material to said first side edge region of said web of bridge material;

(f) attaching said second web of side panel material to said second side edge region of said web of bridge material, said second web of side panel material arranged to provide a cross-directional alignment between at least one corresponding, laterally opposed pair of said first and second fasteners;

(g) dividing said web of bridge material and said first and second webs of side panel material to provide at least one composite bridge assembly having a bridge member interconnecting a laterally opposed pair of first and second side panel members; and (h) securing said composite bridge assembly to an article web with said first fastener and said second fastener of said laterally opposed pair of fasteners located at opposite side regions of said article web.

2. A method as recited in claim 1, wherein said securing step (h) includes the steps of:

(i) providing a web of backsheet material;

(j) positioning at least one absorbent body at a selected location along a machine-direction length of said backsheet web;

(k) providing a web of porous topsheet material to sandwich said absorbent body between said web of backsheet material and said web of topsheet material; and (l) connecting said at least one composite bridge assembly to at least one of said backsheet and topsheet webs, at least a portion of said bridge material arranged in an overlapping relation with a longitudinal end section of said at least one absorbent body.

3. A method as recited in claim 2, wherein said connecting step (l) includes the step of connecting a plurality of said bridge assemblies to at least one of said backsheet and topsheet webs at a plurality of predetermined spaced locations along said machine-direction.

4. A method as recited in claim 2, wherein said connecting step (l) includes the step of securing said composite bridge assembly between said backsheet and topsheet webs and arranging at least a portion of said bridge material to overlap generally adjacent to an inward, bodyside surface of said absorbent body.

5. A method as recited in claim 4, wherein said providing step (b) supplies a bridge material which is constructed to be substantially impermeable to a passage of liquid therethrough.

6. A method as recited in claim 5, wherein said providing step (b) supplies a bridge material which is permeable to a passage of gas therethrough.

7. A method as recited in claim 2, wherein said connecting step (l) includes the step of securing said composite bridge assembly in a substantially adjacent facing relation with a major, bodyside surface of said topsheet web.

8. A method as recited in claim 7, wherein said providing step (b) is arranged to supply a bridge material which is constructed to be substantially impermeable to a passage of liquid therethrough.

9. A method as recited in claim 8, wherein said providing step (b) is arranged to supply a bridge material which is permeable to a passage of gas therethrough.

10. A method as recited in claim 2, further comprising the steps of:

attaching at a pair of lengthwise extending elasticized containment flaps to a bodyside surface of said topsheet web;

attaching said at least one composite bridge assembly to said bodyside of said topsheet web;

arranging at least a portion of said bridge member to overlie said containment flaps in a position interposed between said flaps and a body of a wearer.

11. A method as recited in claim 10, further comprising the steps of:

attaching a longitudinally outboard edge region of said bridge member in a substantially liquid-sealing connection with said topsheet web;

attaching opposing, laterally outboard edge regions of said bridge member in a substantially liquid-sealing connection with said topsheet web;

leaving an inboard edge portion of said bridge member substantially free and unattached.

12. A method as recited in claim 11, further comprising the steps of: arranging said inboard edge portion of said bridge member to span substantially an entire cross-directional distance between said containment flaps to provide a containment pocket.

13. A method for forming an elasticized article, comprising the steps of:

(a) providing first and second webs of elasticized side panel material, said side panel material constructed to be elastically stretchable at least along an appointed lateral, cross-direction, said providing step including the steps of dividing a supply web into said first and second webs of elasticized side panel material, and positioning said first and second webs to a desired spacing therebetween;

(b) attaching a plurality of first fasteners to said first web of side panel material;

(c) attaching a plurality of second fasteners to said second web of side panel material;

(d) providing a web of bridge material having first and second side edge regions thereof;

(e) attaching said first web of side panel material to said first side edge region of said web of bridge material;

(f) attaching said second web of side panel material to said second side edge region of said web of bridge material, said second web of side panel material arranged to provide a cross-directional alignment between a multiplicity of corresponding, laterally opposed pairs of said first and second fasteners;

(g) dividing said web of bridge material and said first and second webs of side panel material to provide a plurality of composite bridge assemblies having a bridge member interconnecting at least one laterally opposed pair of said first and second fasteners; and (h) securing said plurality of composite bridge assemblies to an article web at a plurality of predetermined spaced locations along a machine-directional length of said article web, with each of said laterally opposed pairs of first second fasteners providing first and second fasteners located at opposite side regions of said article web.

14. A method as recited in claim 13, further comprising the steps of:

attaching at a pair of lengthwise extending elasticized containment flaps to a bodyside surface of said topsheet web;

attaching said at least one composite bridge assembly to said bodyside of said topsheet web;

arranging at least a portion of said bridge member overlying said containment flaps in a position interposed between said flaps and a body of a wearer.

15. A method as recited in claim 14, further comprising the steps of:

attaching a longitudinally outboard edge region of said bridge member in a substantially liquid-sealing connection with said topsheet web;

attaching opposing, laterally outboard edge regions of said bridge member in a substantially liquid-sealing connection with said topsheet web;

leaving an inboard edge portion of said bridge member substantially free and unattached.

16. A method as recited in claim 15, further comprising the steps of: arranging said inboard edge portion of said bridge member to span substantially an entire cross-directional distance between said containment flaps to provide a containment pocket.

17. A method as recited in claim 16, wherein said providing step (b) is arranged to supply a bridge material which is constructed to be substantially impermeable to a passage of liquid therethrough.

18. A method as recited in claim 16, wherein said providing step (b) is arranged to supply a bridge material which is permeable to a passage of gas therethrough.

19. A method for forming an elasticized article, comprising the steps of:

(a) providing first and second webs of elasticized side panel material, said side panel material constructed to be elastically stretchable at least along an appointed lateral, cross-direction;

(b) attaching a plurality of first fasteners to said first web of side panel material;

(c) attaching a plurality of second fastener to said second web of side panel material;

(d) providing a separate web of bridge material which is substantially impermeable to the passage of liquid through its thickness, and has first and second side edge regions thereof;

(e) attaching said first web of side panel material to said first side edge region of said web of bridge material;

(f) attaching said second web of side panel material to said second side edge region of said web of bridge material, said second web of side panel material arranged to provide a cross-directional alignment between corresponding, laterally opposed pairs of said first and second fasteners;

(g) dividing said web of bridge material and said first and second webs of side panel material to provide a plurality of composite bridge assemblies having a bridge member interconnecting a laterally opposed pair of first and second side panel members;

(h) providing an article web which includes a web of backsheet material;

(i) positioning a plurality of absorbent bodies at selected locations along a machine-direction length of said backsheet web;

(j) providing a web of porous topsheet material to sandwich said absorbent bodies between said web of backsheet material and said web of topsheet material;

(k) securing said plurality of composite bridge assemblies between said backsheet and topsheet webs, each of said plurality of composite bridge assemblies having at least a portion of the bridge member material arranged to overlap generally adjacent to an inward, bodyside surface of said absorbent body, and having said first fastener and said second fastener of at least one of said laterally opposed pairs of fasteners located at opposite side regions of said article web; and (l) separating said article web along predetermined division lines to provide individual articles.

20. A method as recited in claim 19 wherein said providing step (d) provides an elastomeric bridge material.

21. A method for forming an elasticized article, comprising the steps of:

(a) providing first and second webs of elasticized side panel material, said side panel material constructed to be elastically stretchable at least along an appointed lateral, cross-direction;

(b) attaching a plurality of first fasteners to said first web of side panel material;

(c) attaching a plurality of second fastener to said second web of side panel material;

(d) providing a separate web of bridge material which is elastomeric and has first and second side edge regions thereof;

(e) attaching said first web of side panel material to said first side edge region of said web of bridge material;

(f) attaching said second web of side panel material to said second side edge region of said web of bridge material, said second web of side panel material arranged to provide a cross-directional alignment between corresponding, laterally opposed pairs of said first and second fasteners;

(g) dividing said web of bridge material and said first and second webs of side panel material to provide a plurality of composite bridge assemblies having a bridge member interconnecting a laterally opposed pair of first and second side panel members;

(h) providing an article web which includes a web of backsheet material;

(i) positioning a plurality of absorbent bodies at selected locations along a machine-direction length of said backsheet web;

(j) providing a web of porous topsheet material to sandwich said absorbent bodies between said web of backsheet material and said web of topsheet material;

(k) securing said plurality of composite bridge in a substantially adjacent facing relation with a major, bodyside surface of said topsheet web, each of said plurality of composite bridge assemblies having at least a portion of the bridge member material arranged to overlap with a longitudinal end section of said at least one of said absorbent bodies, and having said first fastener and said second fastener of at least one of said laterally opposed pairs of fasteners located at opposite side regions of said article web; and (l) separating said article web along predetermined division lines to provide individual articles.

22. A method for forming an elasticized article, comprising the steps of:

(a) providing first and second webs of elasticized side panel material, said side panel material constructed to be elastically stretchable at least along an appointed lateral, cross-direction;

(b) attaching a plurality of first fasteners to said first web of side panel material;

(c) attaching a plurality of second fastener to said second web of side panel material;

(d) providing a separate web of bridge material which is elastomeric and has first and second side edge regions thereof;

(e) attaching said first web of side panel material to said first side edge region of said web of bridge material;

(f) attaching said second web of side panel material to said second side edge region of said web of bridge material, said second web of side panel material arranged to provide a cross-directional alignment between corresponding, laterally opposed pairs of said first and second fasteners;

(g) dividing said web of bridge material and said first and second webs of side panel material to provide a plurality of composite bridge assemblies having a bridge member interconnecting a laterally opposed pair of first and second side panel members;

(h) providing an article web which includes a web of backsheet material;

(i) positioning a plurality of absorbent bodies at selected locations along a machine-direction length of said backsheet web;

(j) providing a web of porous topsheet material to sandwich said absorbent bodies between said web of backsheet material and said web of topsheet material;

(k) attaching at a pair of lengthwise extending elasticized containment flaps to a bodyside surface of said topsheet web;

(l) securing said plurality of composite bridge in a substantially adjacent facing relation with a major, bodyside surface of said topsheet web, each of said plurality of composite bridge assemblies located with at least a portion of the bridge member material arranged to overlie said containment flaps in a position interposed between said flaps and a body of a wearer, and having said first fastener and said second fastener of at least one of said laterally opposed pairs of fasteners located at opposite side regions of said article web; and (m) separating said article web along predetermined division lines to provide individual articles.

* * * * *